(12) United States Patent
Rothblat et al.

(10) Patent No.: US 7,402,404 B2
(45) Date of Patent: Jul. 22, 2008

(54) ASSAY METHOD FOR MEASUREMENT OF NET CHOLESTEROL FLUX

(75) Inventors: George H. Rothblat, Philadelphia, PA (US); Ginny Kellner-Weibel, Harleysville, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 322 days.

(21) Appl. No.: 11/116,469

(22) Filed: Apr. 28, 2005

(65) Prior Publication Data

US 2005/0191715 A1    Sep. 1, 2005

Related U.S. Application Data

(63) Continuation-in-part of application No. 10/264,191, filed on Oct. 3, 2002, now Pat. No. 7,060,452.

(60) Provisional application No. 60/326,831, filed on Oct. 3, 2001.

(51) Int. Cl.
*C12Q 1/60* (2006.01)
*G01N 33/92* (2006.01)

(52) U.S. Cl. .......................... 435/11; 436/71
(58) Field of Classification Search ...................... None
See application file for complete search history.

(56) References Cited

OTHER PUBLICATIONS

Stedman's Medical Dictionary, from Dictionary.com, accessed Oct. 18, 2007.*
Rothblat et al., "Cell cholesterol efflux: integration of old and new observations provides new Insights", J. Lipid Research 40 : 781-796 (1999).
Fofana, M., et al., "Transfer of cholesterol between high density lipoproteins and cultured rat Sertoli cells", Biochem. Cell Biol., 74: 681-686 (1996).
Fournier, N., et al., "Fractional efflux and net change in cellular cholesterol content mediated by sera from mice expressing both human apolipoprotein A1 and human lecithin: cholesterol acyltransferase genes", Atherosclerosis, 147: 227-235 (1999).
Atger, V.M., et al., "Cyclodextrins as Catalysts for the Removal of Cholesterol from Macrophage Foam Cells", J. Clin. Invest., vol. 99: 773-780, (1997).
Shio, H., et. al., "Characterization of Lipid-Laden Aortic Cells from Cholesterol-Fed Rabbits"; Lab. Invest. 39: 390-397 (1978).
Small, D. M., "Progression and Regression of Atherosclerotic Lesions"; Arteriosclerosis, 8: 103-129 (1988).
Contreras, J. A., et. al., "Essential Differences in Cholesteryl Ester Metabolism Between Human Monocyte-Derived and J774 Macrophages"; Arterioscler. Thromb. 14: 443-452 (1994).
Hakamata, H., et. al., "Species Difference in Cholesteryl Ester Cycle and HDL-Induced Cholesterol Efflux From Macrophage Foam Cells"; Arterioscler. Thromb. 14: 1860-1865 (1994).
Johnson, W. J., et. al., "Cholesterol transport between cells and high-density lipoproteins"; Biochim. Biophys. Acta. 1085: 273-298 (1991).
Hakamata, H., et. al., "Differential effects of an acyl-coenzyme A:cholesterol acyltransferase inhibitor on HDL-induced cholesterol efflux from rat macrophage foam cells"; FEBS 363: 29-32 (1995).
Johnson, W. J., et. al., "The Bidirectional Flux of Cholesterol between Cells and Lipoproteins"; J. Biol. Chem. 261: 5766-5776 (1986).
Bernard, D. W., et al., "cAMP Stimulates Cholesteryl Ester Clearance to High Density Lipoproteins in J774 Macrophages"; J. Biol. Chem. 266: 710-716 (1991).
Miyazaki, A., et. al., "Acetylated Low Density Lipoprotein Reduces Its Ligand Activity for the Scavenger Receptor after Interaction with Reconstituted High Density Lipoprotein"; J. Biol. Chem. 269: 5264-5269 (1994).

* cited by examiner

*Primary Examiner*—Sandra Saucier
(74) *Attorney, Agent, or Firm*—Dann, Dorfman, Herrell & Skillman; Robert C. Netter; Kathleen D. Rigaut (57) ABSTRACT

The present invention relates to an assay for determining net cholesterol flux from lipid loaded cells in the presence of an acceptor (e.g., serum). The present invention also relates to a method for evaluating efficacy of a therapeutic agent for stimulating or inhibiting net cholesterol flux. Also provided by the present invention are kits that are used to carry out the aforementioned assays and methods.

17 Claims, 10 Drawing Sheets

ASSAY METHOD FOR MEASUREMENT OF NET CHOLESTEROL FLUX

CONTINUING APPLICATION DATA

This application is a continuation-in-part of U.S. Application Ser. No. 10/264,191, now U.S. Pat. No. 7,060,452, filed Oct. 3, 2002, which claims priority under 35 U.S.C. §119(e) to U.S. Provisional Patent Application No. 60/326,831 filed on Oct. 3, 2001. The foregoing applications are incorporated by reference herein.

FIELD OF THE INVENTION

The present invention relates to the fields of diagnostic testing and cholesterol metabolism. More specifically, assays are provided for determining net cholesterol flux.

BACKGROUND OF THE INVENTION

Several publications and patent documents are referenced in this application in order to more fully describe the state of the art to which this invention pertains. Full citations for these references are found within and at the end of the specification. The disclosure of each of these publications is incorporated by reference herein.

Atherosclerosis is a leading cause of death in the United States and results from the formation of plaques in arterial walls that often occlude the vessel lumen and obstruct blood flow. Morbidity and mortality generally occur through end organ damage and organ dysfunction resulting from ischemia. The most common forms of ischemic end organ damage are myocardial infarction and cerebrovascular accidents. Disability or death often result from these vascular events. Atherosclerosis-related ischemia that does not permanently injure myocardium often causes anginapectoris and congestive heart failure. Additionally, atherosclerotic occlusions may damage other organs, such as the kidneys, the intestines, and the spinal cord. These occlusions consist of plaques that form by accumulation of cholesterol, cholesterol esters, and phospholipids and the proliferation of smooth muscle cells in the intima of major arteries. Lipid contributes a major portion of the plaque volume (generally 30-65% dry weight). In fact, the risk of developing arteriosclerosis is directly related to the concentration of certain forms of plasma cholesterol. The reduction of the initiation and progression of atherosclerosis by eliminating accumulation of lipid within vessel walls provides a therapeutically valuable approach for the prevention of cardiovascular disease.

Delivery of cholesterol into cells occurs via the receptor-mediated low density lipoprotein (LDL) pathway and by passive exchange of sterol between plasma membranes and lipoproteins. Only tissues that produce steroid hormones and bile acids can metabolize cholesterol. In order to prevent accumulation of excess free sterol in remaining peripheral tissues there is a reverse transport of cholesterol from plasma membranes into HDL and lipoprotein-like particles. HDL transports excess cholesterol to the liver where it can either be processed into bile salts for excretion or incorporated into very low density lipoproteins (VLDL) to re-enter the lipoprotein pool.

Assays that are currently available to measure cholesterol movement often employ isotopically labeled cholesterol to measure the movement of unesterified cholesterol (free cholesterol, FC) into (influx) or out of (efflux) cells. However, these assays have several disadvantages. First, the movement of cholesterol between cells and serum is bidirectional, thus net cholesterol flux is determined by the relative contribution of cholesterol influx and cholesterol efflux. Currently available assays measure cholesterol efflux only, and therefore fail to account for cholesterol influx. Measurements obtained from these assays could be inaccurate and misleading. Second, because these currently available assays measure the efflux of unesterified cholesterol, they cannot account for the pool of EC in atherogenic cells which is the major form of cholesterol present in foam cells both in vitro and in vivo (3, 4). Finally, inasmuch as non-human macrophage cells are used in such assays, they are not ideally suited for testing therapeutic agents for the treatment of human subjects.

SUMMARY OF THE INVENTION

In accordance with the instant invention, assays for determining net cholesterol flux are provided. In one embodiment, the method comprises the steps of 1) providing detectably labeled cholesterol (e.g. radiolabeled) containing cells; 2) determining a first specific activity for the cholesterol containing cells; 3) exposing the cholesterol containing cells to a cholesterol acceptor (e.g., serum or fraction thereof) and at least one cholesterol synthesis inhibitor (e.g., HMG-CoA reductase inhibitor) for a period of time sufficient enough to allow cholesterol flux to occur; 4) determining cholesterol efflux by measuring the amount of detectably labeled cholesterol in the media; 5) measuring the intracellular cholesterol mass and determining a second specific activity; 6) determining cholesterol influx from the reduction in the second specific activity compared to the first specific activity; and 7) comparing the cholesterol efflux to the cholesterol influx. A net cholesterol efflux is present when cholesterol efflux is greater than the cholesterol influx and a net cholesterol influx is present when cholesterol influx is greater than the cholesterol efflux.

In accordance with another aspect of the instant invention, methods for determining the ability of at least one compound to modulate net cholesterol flux are provided. In a particular embodiment, a first net cholesterol flux is determined for a cholesterol acceptor by the methods described herein. The compound(s) to be tested is then exposed to the cholesterol containing cells along with the cholesterol acceptor and cholesterol synthesis inhibitor and a second net flux is determined by the methods described herein. The first and second net cholesterol fluxes are then compared to determine whether the compound(s) is capable of modulating net cholesterol flux.

In yet another embodiment, additional methods for determining the ability of at least one compound to modulate net cholesterol flux are provided. These methods comprise the steps of 1) obtaining a first cholesterol acceptor sample from a subject; 2) determining a first net cholesterol flux mediated by the first cholesterol acceptor sample by the methods described herein; 3) administering the compound(s) to a subject; 4) obtaining a second cholesterol acceptor sample from the subject after the administration of the compound(s); 5) determining a second net cholesterol flux mediated by the second cholesterol acceptor sample by the methods described herein; and 6) comparing the first and second net cholesterol fluxes. A difference between the second net cholesterol flux and the first net cholesterol flux indicates that the compound(s) is capable of modulating net cholesterol flux.

Kits for practicing the methods described herein are also provided. Exemplary kits contain detectably labeled cholesterol (e.g. radiolabeled) and one or more cholesterol synthesis inhibitors. The kits may further comprise one or more of the following: cell culture media, cell culture tubes or multi-well plates, one or more cholesterol acceptors, instruction material, and reagents used in the measurement of cellular cholesterol mass and labeled cholesterol.

DETAILED DESCRIPTION OF THE INVENTION

The majority of lipid present in early atherosclerotic plaques is in the form of esterified cholesterol (EC) contained within macrophage-derived foam cells. Sensitive net cholesterol flux assays have been developed in accordance with the present invention.

In one embodiment, a macrophage foam cell model is utilized to measure changes in total cholesterol (both EC and FC) mass when exposed to extracellular cholesterol acceptors (e.g., serum). In an alternative embodiment, macrophage cells containing basal levels of cholesterol are utilized in the assay. By incubating these cholesterol "normal" cells with a donor (acLDL) and an acceptor (e.g., serum or isolated lipoprotein) simultaneously, the acceptor's ability to promote or prevent the deposition of donor-derived cellular cholesterol can be evaluated. A standardized assay according to the invention can be used to screen whole sera, isolated lipoproteins, or other sera components from subjects on lipoprotein modifying therapies for the potential to move a measurable amount of cholesterol mass as opposed to the isotopic trace levels measured by traditional flux studies. In a further aspect, data obtained using this assay can be used to advantage in evaluating the effectiveness of lipoprotein modifying pharmaceuticals.

In an exemplary assay, net cholesterol flux is assessed by 1) contacting cholesterol enriched cells with a serum sample (i.e., an acceptor) and 2) quantifying the cellular cholesterol mass from the cholesterol enriched cells after exposure to the serum sample, wherein a reduction of the cellular cholesterol mass compared to that determined prior to the exposure to said serum sample correlates with the cholesterol clearance potential of the serum sample. In a specific embodiment of the present invention, the cholesterol enriched cells are foam cells.

Alternatively, the cholesterol enriched cells are obtained by incubating normal or recombinant cells that express one or more LDL-receptors or scavenger receptor with a cholesterol donor, such as native LDL, acetylated LDL (acLDL), oxidized LDL (oxLDL), aggregated LDL, or derivatives thereof. The cholesterol enriched cells may also be enriched with free cholesterol (unesterified) by culturing with a cholesterol donor in the presence of an acyl CoA:cholesterolacyl transferase (ACAT) inhibitor, including without limitation, CP-113,818 (Pfizer Pharmaceuticals; Groton, Conn.) and 58-035 (Sandoz Pharmaceuticals; Vienna, Austria). In a further embodiment of the present invention, the serum obtained from the subject is the HDL-containing fraction of the serum wherein apoB containing lipoproteins are removed.

Exemplary methods for evaluating efficacy of a therapeutic agent in stimulating or inhibiting net cholesterol flux in a subject comprise the steps of: 1) administering the therapeutic agent to the subject; 2) obtaining a serum sample from the subject after a suitable time period; and 3) determining the effect of the serum sample (acceptor) on net cholesterol mass flux by the assay disclosed above, wherein an increase or reduction of net cholesterol flux compared to that determined prior to the administration of therapeutic agent indicates the capacity of that agent to influence cholesterol flux.

Also provided by the present invention are kits that are used to carry out the assays disclosed herein. Such kits may contain cholesterol enriched cells, culture medium, culture tubes or multi-well plates, and reagents to perform accurate measurement of cellular cholesterol mass.

Suitable therapeutic agents include drugs, prodrugs, nutraceuticals, and ligands that may modulate net cholesterol flux. The therapeutic agent is administered or dosed in accordance with good medicinal practices, taking into account the clinical condition of the individual subject and other factors known to medical practitioners. The "effective amount" for purposes herein refers to that amount of the therapeutic agent which results in a beneficial therapeutic effect (e.g., serum cholesterol reduction).

Cellular cholesterol mass is the level of total cholesterol (FC and EC) present in cells. It may be measured by any suitable assay, including, but are not limited to, enzymatic or chemical based assays. Such assays include Wako enzymatic assay kits for free and total cholesterol (Biochemical Diagnostics; Edgewood, N.J.), and the assay described by Rudel and Morris (Rudel, L. L. and Morris, M. D. (1973) Determination of Cholesterol using o-phthaldehyde, J. Lipid Res., 14:364-366). In one particular embodiment of the present invention, gas-liquid chromatography (GLC) was utilized in measuring the total cholesterol mass.

Definitions

The following definitions are provided to facilitate an understanding of the present invention.

The phrase "net cholesterol flux" refers to the net movement of cholesterol. It is the net result of the relative contribution of both cholesterol influx (in to the cell) and cholesterol efflux (out of the cell). "Net cholesterol mass flux" refers to the net movement of cholesterol mass determined by the changes of cellular cholesterol mass.

"Cholesterol influx" refers to the delivery of cholesterol into cells by any means including via the LDL-receptormediated LDL pathway and by passive exchange of sterol between plasma membranes and lipoprotein.

"Cholesterol efflux" refers to the reverse transport of cholesterol from plasma membranes into HDL and lipoprotein-like particles.

"Cellular cholesterol mass" is the total cellular cholesterol level and includes both esterified (EC) and unesterified cholesterol (FC).

The phrase "a subject" as used herein refers to both humans and other mammals. The term includes, but is not limited to, mammalian, bovine, ovine, porcine, equine, rodent and human subjects.

"Cholesterol enriched cells" are cells that retain a cellular cholesterol level of about 80-100 µg/mg cell protein. Preferred cell types are macrophage cells, including both primary and transformed macrophage cells. The cells may be of human or non-human origin. Examples of non-human macrophage cells include, but are not limited to, JC774 mouse macrophage cells (ATCC# HB-197), RAW 264.7, primary mouse macrophages from wild type and transgenic mice. Examples of human macrophage cells include, but are not limited to, primary macrophage cells, THP-1 or THP-2 cells (ATCC# TIB-202), U937 (ATCC# CRL-1593.2), and primary human macrophages. Alternatively, cells that are transfected with one or more LDL-receptor genes may be used in this assay. The cells with basal level of cellular cholesterol may be cholesterol enriched by culturing with cholesterol donors.

A "cholesterol donor" is a compound (e.g., a lipoprotein) that delivers cholesterol into cells. Typically, this delivery is via the receptor-mediated LDL pathway. Suitable cholesterol donors include, but are not limited to, acetyl LDL (acLDL), oxidized (oxLDL), native LDL, aggregated LDL, and derivatives thereof.

As used herein, the term "cholesterol acceptor" refers to a compound or composition (e.g. a mixture comprising one or more cholesterol acceptors) which can accept cholesterol from a cell. Cholesterol acceptors include, without limitation, cyclodextrins, β-cyclodextrins, phospholipids vesicles (e.g., small unilamellar vesicles (SUV), large unilamellar vesicles (LUV), multilamellar vesicles (MLV)), lipid-free or lipid-poor apolipoproteins, apoA-I, apoA-IV, apoE, high density liporproteins (HDL), whole serum, plasma, serum fractions, and serum components.

The term "specific activity" refers to the number of activity units per unit of mass, volume, or molarity.

An "ACAT inhibitor" is a compound that inhibits the acyl CoA:cholesterolacyl transferase (ACAT) from esterifying free cholesterol. Compounds that have ACAT inhibiting activity include, but are not limited to, CP-113,818 (Pfizer Pharmaceuticals) and 58-035 (Sandoz Pharmaceuticals).

The term "therapeutic agent" refers to any agent given to a subject to treat, ameliorate or prevent atherosclerosis or other cholesterol or lipid-related disorders. Exemplary agents include, but are not limited to, cholesterol lowering drugs such as Lipitor®.

The term "cholesterol synthesis inhibitor" refers to any agent which inhibits cholesterol synthesis (e.g., HMG-CoA reductase inhibitors).

The term "HMG-CoA reductase inhibitor" refers to 3-hydroxy-3-methylglutaryl coenzyme A inhibitors. Examples include, without limitation, Epistatin, Eptastatin, Mevinolin, Synvinolin, mevastatin (U.S. Pat. No. 3,983,140), lovastatin (Mevacor), mevinolin (U.S. Pat. No. 4,231,938), pravastatin (Pravachol®, U.S. Pat. Nos. 4,346,227 and 4,410,629), lactones of pravastatin (U.S. Pat. No. 4,448,979), velostatin, simvastatin (Zocor®, U.S. Pat. Nos. 4,448,784 and 4,450,171), rivastatin, fluvastatin (Lescol), atorvastatin (Lipitor®), and cerivastatin (Baycol). For other examples of HMG-CoA reductase inhibitors, see U.S. Pat. Nos. 5,217,992; 5,196,440; 5,189,180; 5,166,364; 5,157,134; 5,110,940; 5,106,992; 5,099,035; 5,081,136; 5,049,696; 5,049,577; 5,025,017; 5,011,947; 5,010,105; 4,970,221; 4,940,800; 4,866,058; 4,686,237; 4,647,576; European Application Nos. 0142146A2 and 0221025A1; and PCT Application Nos. WO 86/03488 and WO 86/07054.

Cholesterol Clearance Potential

The movement of cholesterol from cells to serum or interstitial fluid, known as reverse cholesterol transport, is mediated primarily through the action of HDL, a cholesterol acceptor, coupled with serum enzymes such as cholesterol ester transfer protein and lecithin cholesterol acyl-transferase (LCAT). It has been proposed that this reverse cholesterol transport function of HDL imparts its protective effects against the development of atherosclerosis. Great efforts have been made to develop pharmaceutical agents that modify the lipoprotein profile in the serum, therefore stimulating the cholesterol clearance.

According to the present invention, a standard assay is developed to determine the cell cholesterol clearance potential of a serum sample. More specifically, the assay is carried out by exposing cholesterol enriched cells to a serum sample obtained from a subject and quantifying net cholesterol flux in the cholesterol enriched cells after the exposure to the serum sample, wherein a reduction of the cellular cholesterol mass compared to that determined prior to the exposure correlates with the cholesterol clearance potential of the serum sample. Such serum may be assayed before and after administration of a cholesterol lowering drug to said subject. This approach facilitates analysis of the efficacy of the cholesterol lowering drug. Alternatively, the HDL-containing fraction of the serum sample, wherein apoB containing lipoproteins are removed, is used in the present invention.

Also provided herein are kits that are used to carry out the assay presented herein. These kits generally contain cholesterol enriched cells, cell culture media, cell culture tubes or multi-well plates, and reagents used in the measurement of cellular cholesterol mass. In one embodiment of the present invention, a kit may comprise cells that retain one or more LDL-receptors on their cell surfaces, a cholesterol donor, cell culture media, labeled cholesterol, cell culture tubes or multi-well plates, reagents used in the measurement of cellular cholesterol mass, and reagents suitable for the isolation of macrophage. Alternatively, the kit may further comprise an ACAT inhibitor.

Method to Measure Net Cholesterol Flux

In accordance with another aspect of the instant invention, cholesterol influx and efflux can be measured to determine cholesterol exchange. Specifically, cells are labeled with detectably labeled cholesterol. Examples of detectable labels include, without limitation: biotins, avidins, fluorescent compounds (e.g., NBD), radioisotopes, and enzymes. Preferably, the cholesterol is radiolabeled (e.g., $^3$H, $^{125}$I, $^{35}$S, $^{14}$C, and $^{32}$P). An acyl-CoA:cholesterol acyltransferase inhibitor is present during the labeling process to prevent the generation of cholesteryl esters. Any cell of any origin can be used in the assay. Following an equilibration period, time zero cells are collected before cholesterol efflux. The skilled artisan is aware of a variety of methods for quantifying labeled cholesterol. In cases where radiolabels are employed, both cholesterol mass and total cpm are determined and the specific activity at time zero is calculated as cpm/µg cholesterol.

Remaining cells are then incubated with one or more cholesterol acceptors in the presence of at least one cholesterol synthesis inhibitor (e.g., an HMG-CoA reductase inhibitor) to block cholesterol synthesis. Cholesterol efflux is measured by the release of the labeled cholesterol into the medium. The percent efflux of labeled cholesterol times the initial mass of cholesterol provides an estimate of the mass of cell cholesterol released to the acceptors. After the efflux period, the intracellular cholesterol mass is determined and the cholesterol influx is estimated from the reduction in the specific activity compared to the time zero specific activity. Based on these measurements the net cholesterol movement can be expressed as an influx to efflux ratio. Ratios <1 indicate net cholesterol efflux, whereas ratios >1 reflect a net cholesterol influx. Cholesterol exchange without significant net flux is reflected by a ratio=1. Table 1 provides a hypothetical analysis.

TABLE I

| Time zero | |
|---|---|
| Cellular cholesterol content/sample | 10 µg |
| Specific Activity (cpm/µg) | 100,000 |
| After efflux | |
| Percentage efflux | 20% |
| Cholesterol efflux (µg)/sample | 10 µg × 20% = 2 µg |
| Theoretical cholesterol mass after efflux = µg cholesterol at time zero/sample − cholesterol efflux (µg)/sample (assuming no influx) | 10 µg − 2 µg = 8 µg |
| Final Specific Activity (cpm/µg) | 80,000 |
| Specific activity factor: Specific Activity at time zero/final Specific Activity | 100,000 cpm/µg cholesterol ÷ 80,000 cpm/µg cholesterol = 1.25 |
| Calculated cholesterol mass: theoretical cholesterol mass times Specific Activity factor | 8 µg × 1.25 = 10 µg |
| Cholesterol influx (µg)/sample = Calculated cholesterol mass minus Theoretical cholesterol mass | 10 µg − 8 µg = 2 µg |
| RATIO INFLUX/EFFLUX (cholesterol exchange) | 2 µg/2 µg = 1 (no net change in content) |

The above described method can be used to screen compounds for their ability to modulate net cholesterol flux. In one embodiment, the method comprises 1) determining a first net cholesterol flux mediated by a cholesterol acceptor, 2) determining a second net cholesterol flux mediated by the cholesterol acceptor and at least one compound added (e.g., by adding the cholesterol acceptor, the compound(s), and cholesterol synthesis inhibitor to labeled cells prior to measuring efflux), and 3) comparing the first and second net cholesterol fluxes to determine if the compound(s) increases or decreases net cholesterol flux.

Alternatively, the ability of the at least one compound to modulate net cholesterol flux may be studied partly in vivo. For example, a cholesterol acceptor sample (preferably a serum sample) may be isolated from a subject and a first net cholesterol flux can be determined by the above method. The compound(s) may then be administered to the subject. Subsequently, another cholesterol acceptor sample can be obtained from the subject and a second net cholesterol flux can be determined. The first and second net cholesterol fluxes are compared to determine the ability of the compound(s) to modulate net cholesterol flux.

Also provided herein are kits that are used to carry out the assay presented herein. These kits contain at least one of the following: detectably labeled cholesterol (e.g., radiolabeled cholesterol such as [$^3$H]-cholesterol), cell culture media, cells (e.g., macrophage), one or more cholesterol synthesis inhibitors, cell culture tubes or multi-well plates, one or more cholesterol acceptors, instruction material, reagents used in the measurement of cellular cholesterol mass and labeled cholesterol, and reagents suitable for the isolation of macrophage.

The following examples are provided to illustrate an embodiment of the invention. They are not intended to limit the invention in any way.

EXAMPLE I

Cholesterol Clearance Assay

Figure 1:
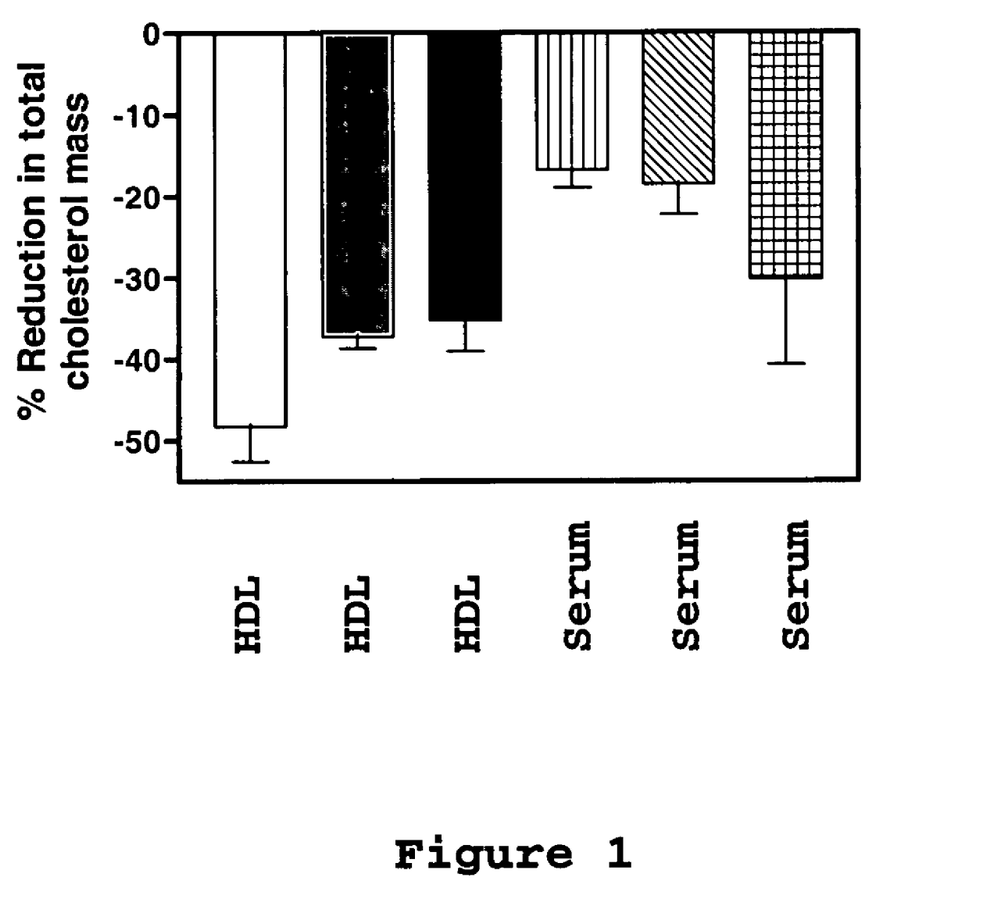
FIG. 1 is a graph showing the results obtained following incubation of THP-2 macrophage foam cells with various acceptors (e.g., HDL and serum). Values are expressed as percent change (decrease) relative to acLDL alone (no acceptor) which was set at zero.

The feasibility of this cholesterol clearance assay using human serum and HDL isolated from human plasma was investigated. In these series of experiments, THP-1 macrophage cells were enriched with cholesterol (basal level=20 µg cholesterol/mg cell protein, enriched 80-100 µg cholesterol/mg cell protein) by incubation with acLDL (100 µg/ml) for 48 hours. The cells were then incubated with 10% human serum or 50 µg/ml HDL for 48 hours. Cholesterol mass was measured by GLC and values were normalized to total cell protein levels. The data represented in FIG. 1 are from experiments performed using a single pool of human serum collected from healthy individuals or a single batch of HDL isolated from fresh human plasma.

EXAMPLE II

Correlation to HDL Parameters

Figure 2:
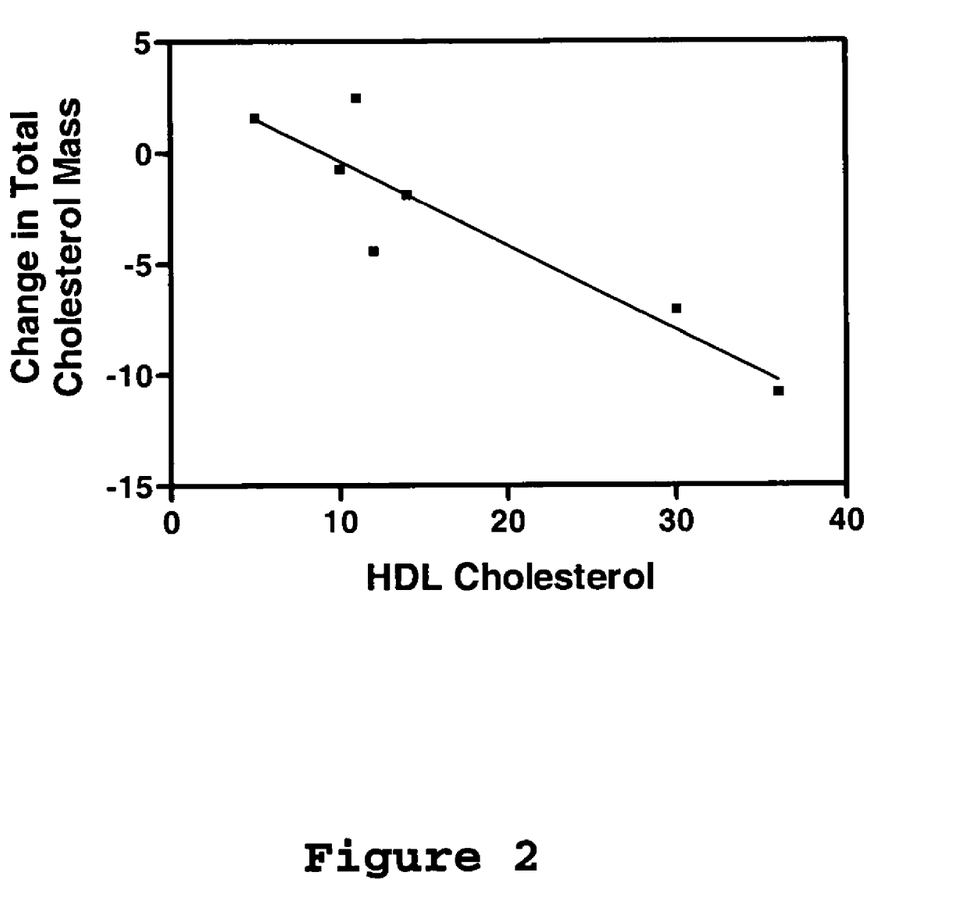
FIG. 2 is a graph showing the correlation between reduction in cellular cholesterol mass and increasing HDL cholesterol concentration levels. Values are expressed as percent change relative to acLDL alone (no acceptor) set at zero.
Figure 3:
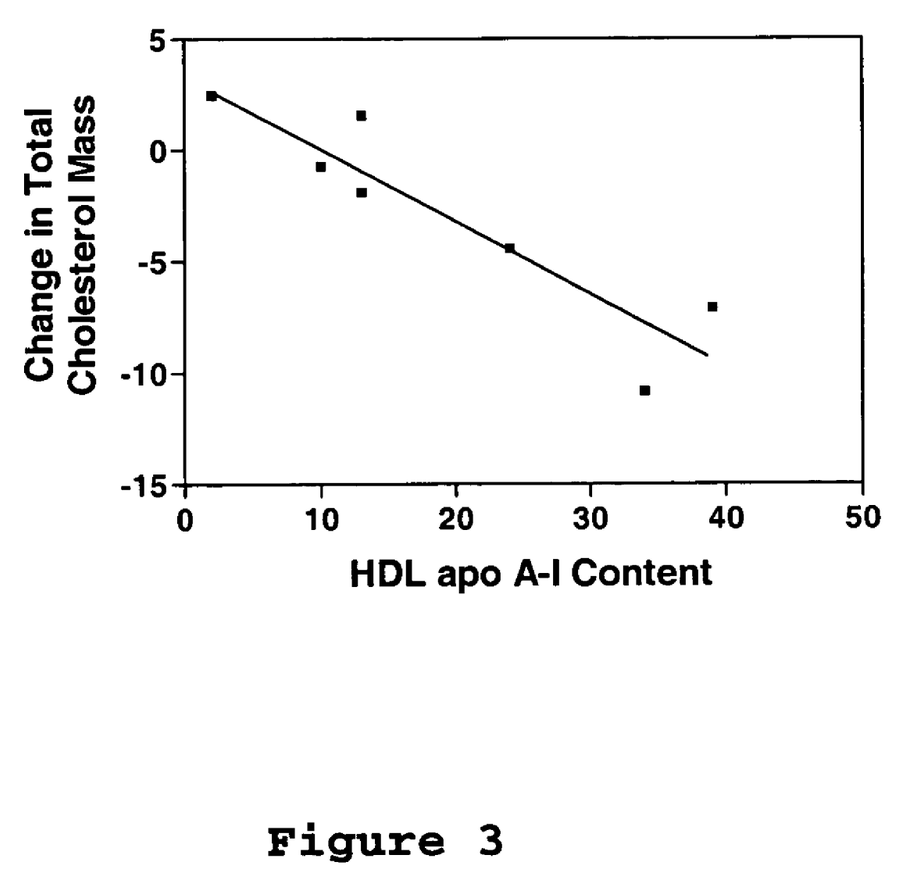
FIG. 3 is a graph showing the correlation between reduction in cellular cholesterol mass and increasing HDL apolipoprotein A-I concentration levels. Values are expressed as percent change relative to acLDL alone (no acceptor) set at zero.

The assay of the present invention provides an accurate assessment of differences in human serum samples with varying HDL concentrations. THP-1 macrophage cells were cholesterol enriched with 100 µg/ml acLDL for 48 hours. The cells were then incubated with 10% human serum (diluted into tissue culture media) from 7 individuals for 48 hours. Cholesterol mass was measured by GLC and values were normalized to total cell protein. FIGS. 2 and 3 demonstrate the correlation between cellular cholesterol mass reduction and serum HDL cholesterol concentration (FIG. 2; $r^2$=0.84) and HDL apolipoprotein A-I concentration (FIG. 3; $r^2$=0.84). Thus, this assay is useful in determining the contribution of different acceptors on cholesterol clearance between clinical samples.

EXAMPLE III

Cholesterol Clearance Assay in Unesterified Cholesterol-Enriched Cells

In a further embodiment of the invention, a net cholesterol flux assay that can be utilized to measure unesterified cholesterol mass reduction from THP-1 macrophage cells was developed. This assay is efficient, cost effective, and can be used when a researcher does not necessarily desire to have esterified cholesterol in the cells. In this system, THP-1 macrophage cells are incubated with free cholesterol/phospholipid dispersions in the presence of an acyl CoA:cholesterol acyl transferase (ACAT) inhibitor. This allows for the accumulation of unesterified cholesterol without allowing ACAT function, the enzyme that is responsible for the esterification of cholesterol to function. The unesterified cholesterol content of the cells increases from 20 µg cholesterol/mg cell protein to 60-70 µg cholesterol/mg cell protein, with no detectable esterified cholesterol. Additionally, the cholesterol enrichment period is 24 hours, compared to the 48 hours used in the assay with esterified cholesterol. After an equilibration period, the cells are exposed to an acceptor for 8-24 hours.

Figure 4:
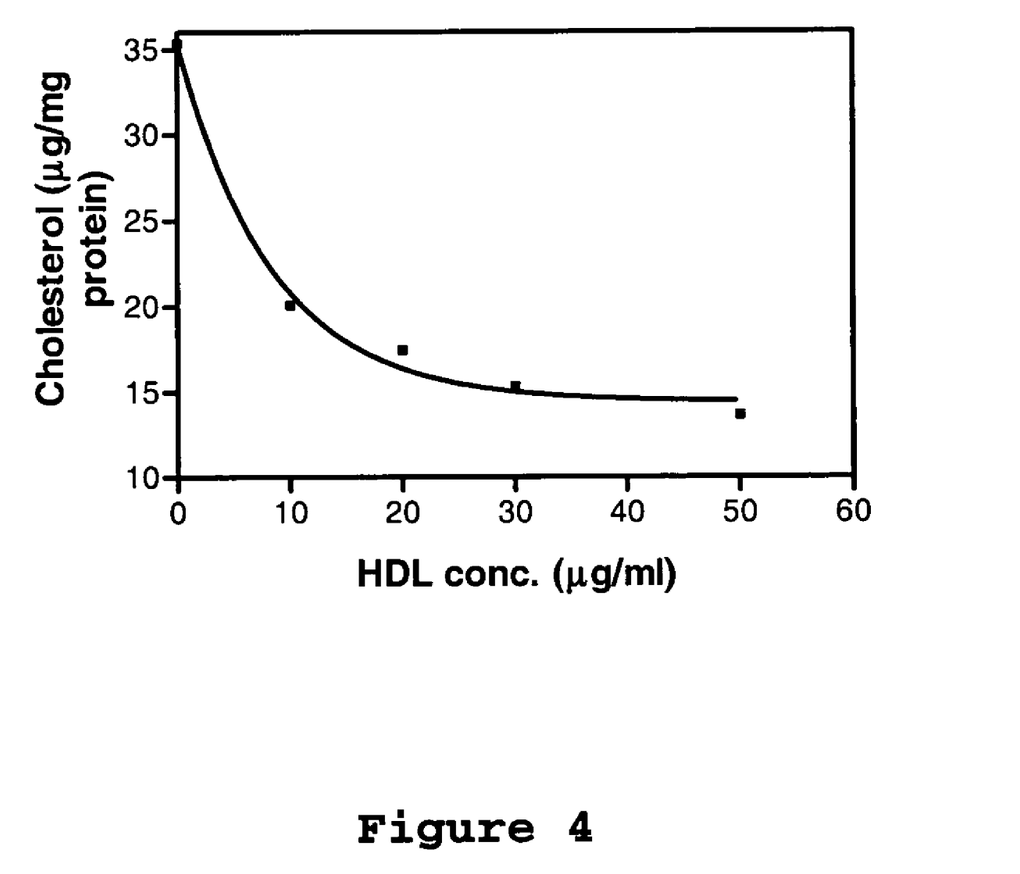
FIG. 4 is a graph showing unesterified cholesterol clearance. Values are expressed as mass of unesterified cholesterol per mg of cell protein.

Like the assay described in the previous example, FIG. 4 shows that this assay is sensitive over a range of HDL concentrations. Specifically, THP-1 macrophage cells were cholesterol enriched with unesterified cholesterol/phospholipid dispersions (250 μg cholesterol/ml) and the ACAT inhibitor CP-113,818 (Pfizer Pharmaceuticals) for 24 hours. The cells were then incubated with human $HDL_3$ at the indicated concentrations for 24 hours (FIG. 4). Cholesterol mass was measured by GLC and values were normalized to cell protein.

EXAMPLE IV

Figure 5:
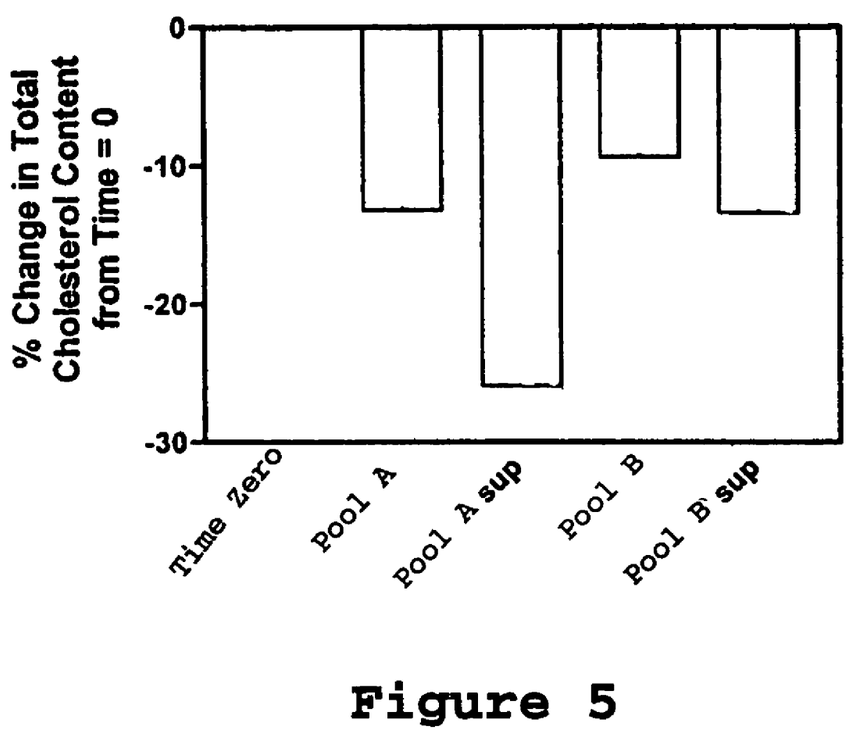
FIG. 5 is a graph showing the effects of the incubation of various acceptors with THP-1 macrophage foam cells on cholesterol flux. Values are expressed as percent change relative to acLDL alone (no acceptor) set at zero.

The Use of Cholesterol Clearance Assay with ApoB Lipoprotein Deprived Clinical Samples In this example, cholesterol enriched THP-1 macrophage cells are incubated for 48 hours with HDL-containing supernatant following removal of apoB lipoprotein. Specifically, THP-1 macrophage cells were cholesterol enriched with 100 μg/ml acLDL for 48 hours. The cells were then incubated with 10% of the supernatant generated after precipitating the apoB containing lipoprotein with PEG for 48 hours. Cholesterol mass was measured by GLC and values were normalized to cell protein. FIG. 5 shows the results from such an experiment. As shown, both pools of human serum tested caused a significant decrease (9-13%) in the mass of cholesterol in the THP-1 foam cells. Furthermore, both HDL-containing supernatants lacking apoB were more effective (13-27%) in promoting cholesterol clearance than their corresponding whole serum samples.

EXAMPLE V

Improved Protocol for Removing ApoB Lipoproteins from Serum

Figure 6:
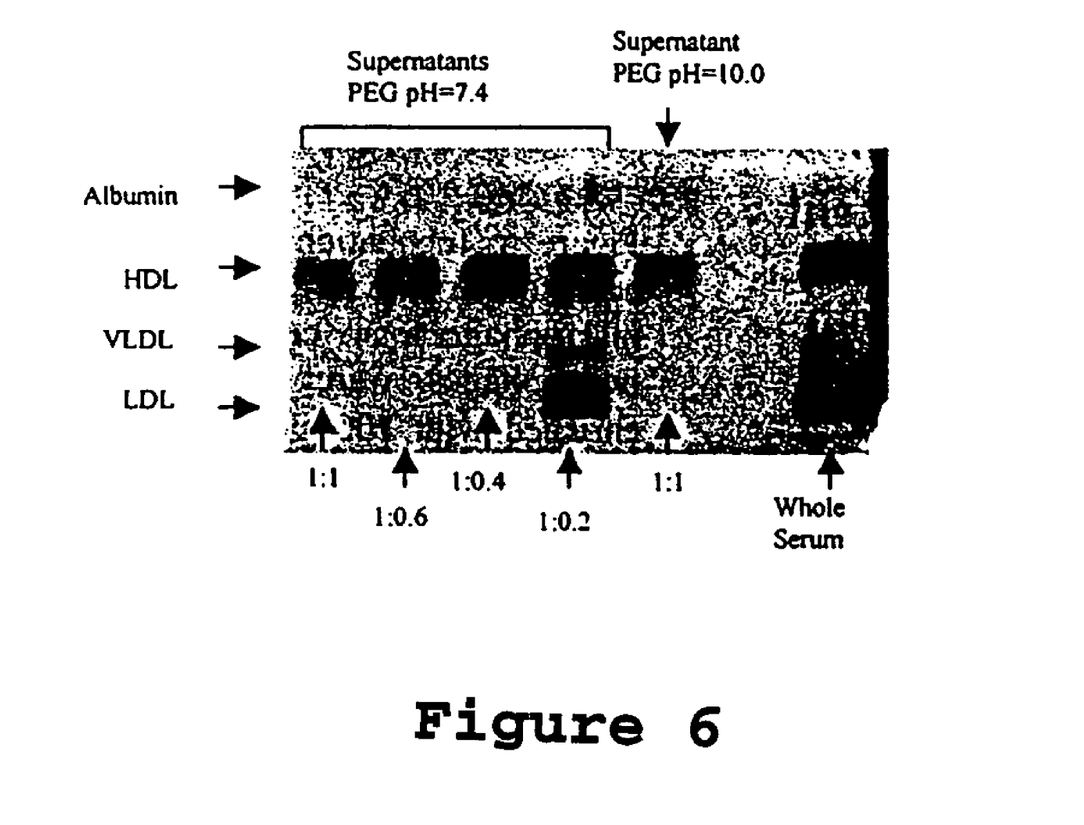
FIG. 6 is a gel demonstrating removal of LDL and VLDL with PEG.

The supernatant generated from precipitation of apoB containing lipoprotein is not toxic to cells and does not interfere with the uptake of acLDL into THP-1 macrophage cells. One complication associated with this procedure is exposing serum to the high pH required to solubilize PEG (pH=10). The published procedure was modified and the pH of the PEG reagent was adjusted to 7.4 prior to serum addition. Specifically, a 20% PEG solution (pH=10.0 or 7.4) was added to serum at a 1:1, 1:0.6, 1:0.4, or 1:0.2 (serum to reagent) ratio and incubated at room temperature for 15 minutes. The solution was then centrifuged at 4000 rpm (1900 g) for 20 minutes at 4° C. The supernatant were run on a LipoGel system (Beckman Coulter, Fullerton, Calif.). FIG. 6 illustrates that this process effectively removed LDL and VLDL from the serum. Additionally, the amount of reagent added to the serum sample can be reduced to a 1:0.4 (serum to reagent) ratio and still effectively remove the LDL and VLDL.

EXAMPLE VI

Determining Net Cholesterol Flux

FU5AH hepatoma cells were plated in 12-well plates at a density of $6\times10^5$ cells/well. The following day, cell monolayers were labeled for 24 hours with 3 μCi/ml [$^3$H]-cholesterol in 2.5% calf serum-containing medium in the presence of 2 μg/ml acyl CoA cholesterol acyltransferase inhibitor. Following an equilibration period in 0.2% BSA-containing medium, time zero cells were collected before cholesterol efflux. Both cholesterol mass and total counts per minute (cpm) were determined and the specific activity at time zero was calculated as cpm/μg cholesterol.

The remaining monolayers were then incubated with whole human sera from normolipidemic individuals or fractions thereof (diluted to 2.5% in medium) as cholesterol acceptors for 8 hours in the presence of 2 μg/ml of the HMG-CoA reductase inhibitor mevinolin to block cholesterol synthesis. To separate the HDL fraction from the ApoB-containing lipoprotein fraction, an aliquot of every whole serum was incubated for 20 min in 20% polyethylene glycol solution with 200 mM glycine. The samples were then centrifuged at 4° C. for 30 minutes at 10,000 rpm and the supernatant, representing the ApoB-depleted serum, was collected. The ApoB-containing lipoproteins (such as LDL and VLDL) contribution was determined by subtracting the HDL contribution from the value obtained from whole serum.

Figure 7A:
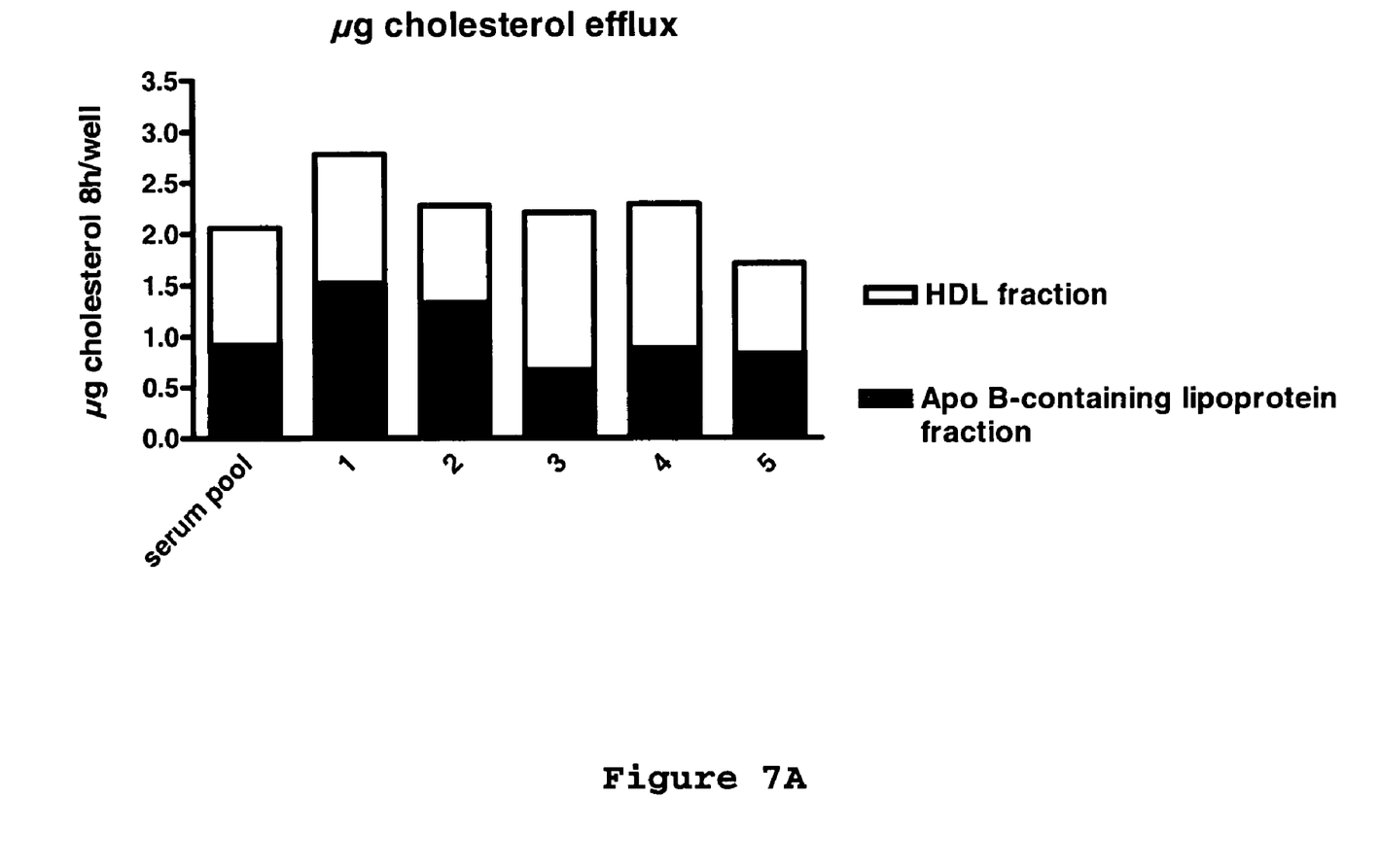
FIGS. 7A-7C are graphs demonstrating cholesterol efflux (FIG. 7A), cholesterol influx (FIG. 7B), or net cholesterol flux from FU5AH cells contacted with the cholesterol acceptors of whole human serum or fractions of human serum.
Figure 7B:
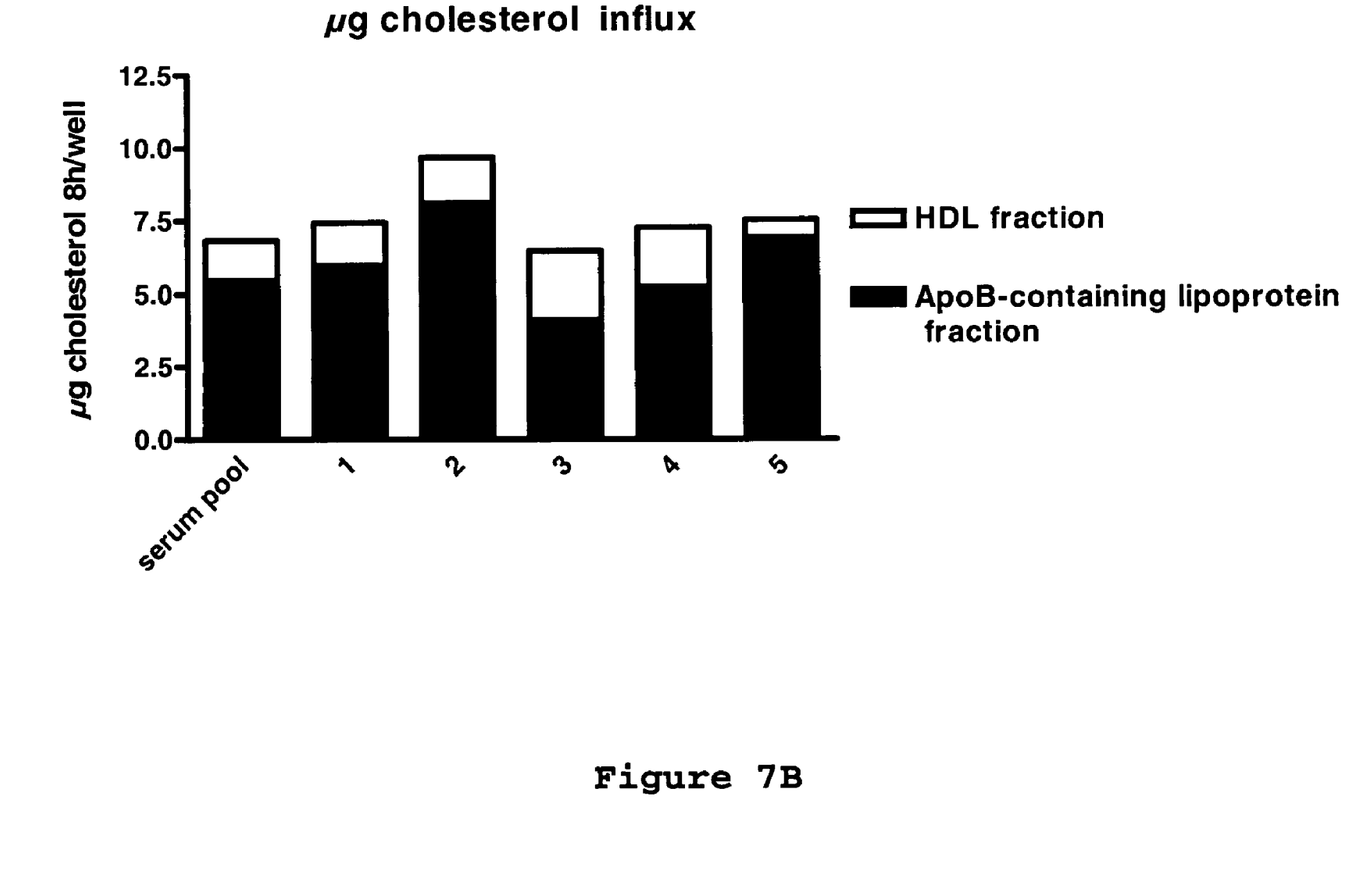
Figure 7C:
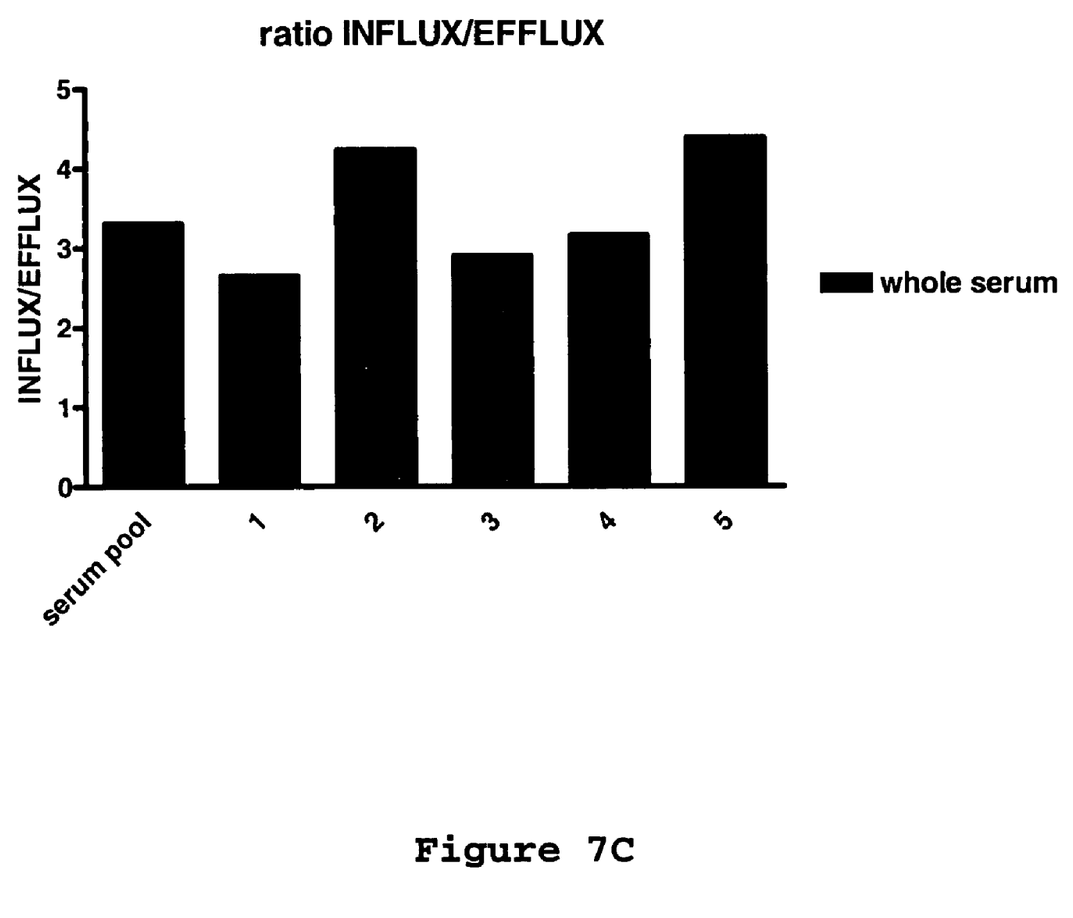

Cholesterol efflux was measured by the release of [$^3$H]-cholesterol into the medium. The percent efflux of labeled cholesterol times the initial mass of cholesterol provides an estimate of the mass of cell cholesterol released to the acceptors (FIG. 7A). After the efflux period the intracellular cholesterol mass was determined and the cholesterol influx was estimated from the reduction in the specific activity compared to time zero specific activity (FIG. 7B). Based on these measurements the net cholesterol movement for whole serum was expressed as an influx to efflux ratio (FIG. 7C).

Figure 8A:
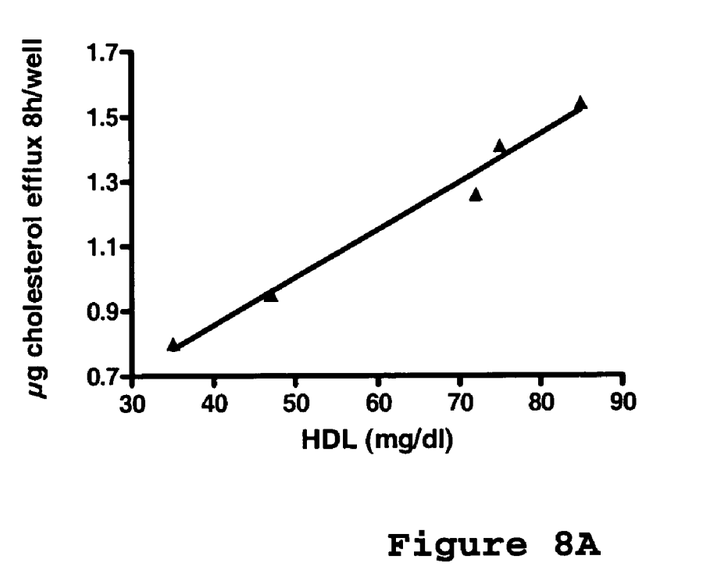
FIGS. 8A and 8B are graphs showing the correlation between cholesterol efflux (FIG. 8A) and cholesterol influx (FIG. 8B) and plasma HDL levels.
Figure 8B:
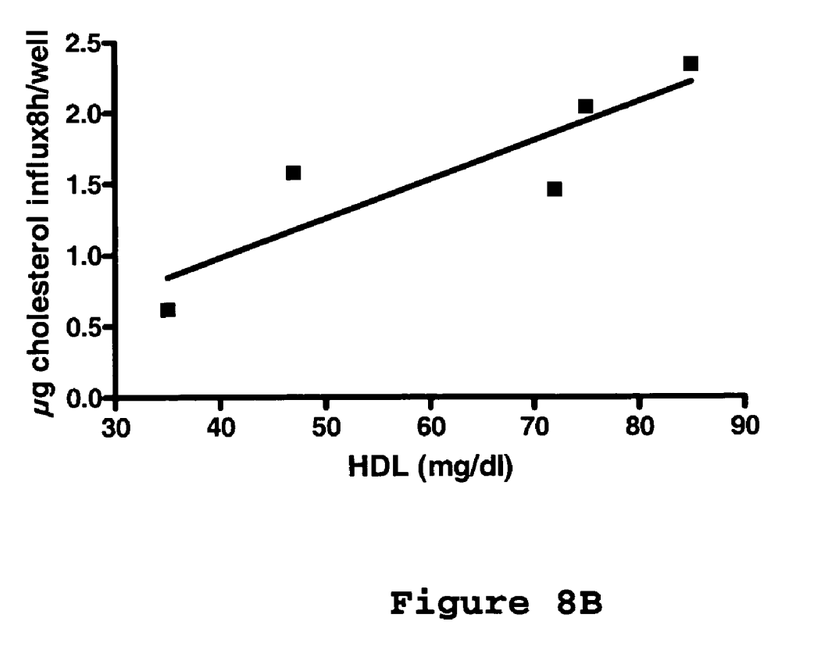

FIGS. 8A and 8B represent results of experiments, as described above, wherein the cholesterol acceptor was sera samples from 5 normal individuals comprising varying concentrations of HDL. Notably, as HDL concentration increased, the efflux and influx of cholesterol also increased.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

REFERENCES

1. Johnson, W. J., F. H. Mahlberg, G. H. Rothblat, and M. C. Phillips. 1991. Cholesterol transport between cells and high density lipoproteins. *Biochim. Biophys. Acta* 1085: 273-298.
2. Johnson, W. J., M. J. Bamberger, M. J. Latta, R. A. Rapp, M. C. Phillips, and G. H. Rothblat. 1986. The bidirectional flux of cholesterol between cells and lipoproteins. *J. Biol. Chem.* 261:5766-5776.
3. Small, D. M. 1988. Progression and regression of atherosclerotic lesions. *Artero.* 8:103-129.
4. Shio, H., N. J. Haley, and S. Fowler. 1978. Characterization of Lipid-laden aortic cells from cholesterol-fed rabbits II. Morphometric analysis of lipid-filled lysosomes and lipid droplets in aortic cell population. *Laboratory Investigation* 39:390-397.
5. Hakamata, H., A. Miyazaki, M. Sakai, Y. Suginohara, Y.-I. Sakamoto, and S. Horiuchi. 1994. Species difference in cholesteryl ester cycle and HDL-induced cholesterol efflux from macrophage foam cells. *Arterioscler. Thromb.* 14:1860-1865.
6. Bernard, D. W., A. Rodriguez, G. H. Rothblat, and to J. M. Glick. 1991. cAMP stimulates cholesteryl ester clearance to high density lipoproteins in J774 macrophages. *J. Biol. Chem.* 266:710-716.

7. Contreras, J. A. and M. A. Lasunción. 1994. Essential differences in cholesteryl ester metabolism between human monocyte-derived and J774 macrophages: Evidence against the presence of hormone-sensitive lipase in human macrophages. *Arterioscler. Thromb.* 14:443-452.
8. Hakamata, H., A. Miyazaki, M. Sakai, Y.-I. Sakamoto, H. Matsuda, K. Kihara, and S. Horiuchi. 1995. Differential effects of an acyl-coenzyme A:cholesterol acyltransferase inhibitor on HDL-induced cholesterol efflux from rat macrophage foam cells. *FEBS* 363:29-32.
9. Miyazaki, A., M. Sakai, Y. Suginohara, H. Hakamata, Y.-I. Sakamoto, W. Morikawa, and S. Horiuchi. 1994. Acetylated low density lipoprotein reduces its ligand activity for the scavenger receptor after interaction with reconstituted high density lipoprotein. *J. Biol. Chem.* 269:5264-5269.

What is claimed is:

1. A method for determining net cholesterol flux from cholesterol containing cells following exposure to a cholesterol acceptor, comprising the steps of:
    a) providing detectably labeled cholesterol containing cells;
    b) determining a first specific activity for said cholesterol containing cells;
    c) exposing said cholesterol containing cells to a cholesterol acceptor and at least one cholesterol synthesis inhibitor for a period of time sufficient enough to allow cholesterol flux to occur;
    d) determining cholesterol efflux by measuring the amount of detectably labeled cholesterol in the media;
    e) measuring the cellular cholesterol mass and determining a second specific activity;
    f) determining cholesterol influx from the reduction in said second specific activity compared to said first specific activity; and
    g) comparing said cholesterol efflux to said cholesterol influx, wherein a net cholesterol efflux is present when cholesterol efflux is greater than the cholesterol influx and wherein a net cholesterol influx is present when cholesterol influx is greater than the cholesterol efflux.

2. The method of claim 1, wherein said detectably labeled cholesterol is radiolabeled cholesterol.

3. The method of claim 2, wherein said radiolabeled cholesterol is [$^3$H]-cholesterol.

4. The method of claim 1, wherein said cholesterol acceptor is serum or a fraction thereof.

5. The method of claim 4, wherein said cholesterol acceptor is serum.

6. The method of claim 4, wherein said cholesterol acceptor is the HDL fraction of serum.

7. The method of claim 1, wherein said at least one cholesterol synthesis inhibitor comprises at least one HMG-CoA reductase inhibitor.

8. The method of claim 7, wherein said HMG-CoA reductase inhibitor is selected from the group consisting of epistatin, eptastatin, mevinolin, synvinolin, mevastatin, lovastatin, mevinolin, pravastatin, lactones of pravastatin, velostatin, simvastatin, rivastatin, fluvastatin, atorvastatin, and cerivastatin.

9. The method of claim 8, wherein said HMG-CoA reductase inhibitor is mevinolin.

10. A method for determining the ability of at least one compound to modulate net cholesterol flux, said method comprising the steps of:
    a) determining a first net cholesterol flux by the method of claim 1;
    b) determining a second net cholesterol flux in the presence of said at least one compound; and
    c) comparing said first and second net cholesterol flux, wherein an alteration of said second net cholesterol flux compared to said first net cholesterol flux indicates the ability of said at least one compound to modulate net cholesterol flux.

11. The method of claim 10, wherein said at least one compound causes an increase in cholesterol efflux.

12. The method of claim 10, wherein said at least one compound causes an increase in cholesterol influx.

13. A method for determining the ability of at least one compound to modulate net cholesterol flux, said method comprising the steps of:
    a) obtaining a first cholesterol acceptor sample from a subject;
    b) determining a first net cholesterol flux mediated by said first cholesterol acceptor sample by the method of claim 1;
    c) administering said at least one compound to said subject;
    d) obtaining a second cholesterol acceptor sample from said subject after the administration of said at least one compound;
    e) determining a second net cholesterol flux mediated by said second cholesterol acceptor sample by the method of claim 1; and
    f) comparing said first and second net cholesterol flux, wherein an alteration of said second net cholesterol flux compared to the first net cholesterol flux indicates the capacity of said at least one compound to modulate net cholesterol flux.

14. The method of claim 13, wherein said at least one compound causes an increase in cholesterol efflux.

15. The method of claim 13, wherein said at least one compound causes an increase in cholesterol influx.

16. The method of claim 13, wherein said cholesterol acceptor sample is a serum sample.

17. The method of claim 13, wherein said cholesterol acceptor sample is diluted prior to determining net cholesterol flux.

* * * * *